(12) United States Patent
Meier et al.

(10) Patent No.: US 11,525,820 B2
(45) Date of Patent: Dec. 13, 2022

(54) MANUFACTURING FLUID SENSING PACKAGES

(71) Applicant: TEXAS INSTRUMENTS INCORPORATED, Dallas, TX (US)

(72) Inventors: Sebastian Meier, Munich (DE); Heinrich Wachinger, Helfenbrunn (DE); Bernhard Peter Lange, Freising (DE)

(73) Assignee: TEXAS INSTRUMENTS INCORPORATED, Dallas, TX (US)

(*) Notice: Subject to any disclaimer, the term of this patent is extended or adjusted under 35 U.S.C. 154(b) by 0 days.

(21) Appl. No.: 16/572,303

(22) Filed: Sep. 16, 2019

(65) Prior Publication Data

US 2020/0185282 A1    Jun. 11, 2020

Related U.S. Application Data

(60) Provisional application No. 62/776,236, filed on Dec. 6, 2018.

(51) Int. Cl.
*G01N 33/18* (2006.01)
*G01N 27/07* (2006.01)
*G01N 27/08* (2006.01)
*H01L 21/67* (2006.01)

(52) U.S. Cl.
CPC ......... *G01N 33/1886* (2013.01); *G01N 27/07* (2013.01); *G01N 27/08* (2013.01); *G01N 33/1893* (2013.01); *H01L 21/6715* (2013.01)

(58) Field of Classification Search
CPC .... G01N 27/07; G01N 27/08; G01N 33/1886; G01N 33/1893
See application file for complete search history.

(56) References Cited

U.S. PATENT DOCUMENTS

| | | | | |
|---|---|---|---|---|
| 4,927,188 | A * | 5/1990 | Sands | F16L 41/00 285/136.1 |
| 10,760,853 | B1 * | 9/2020 | Chandler | F16K 1/12 |
| 2007/0211244 | A1 * | 9/2007 | Hilmer | G01N 30/74 356/246 |
| 2012/0143531 | A1 * | 6/2012 | Davey | G01N 33/48785 73/40.5 R |
| 2013/0255572 | A1 * | 10/2013 | Nettesheim | B65D 85/00 118/600 |

(Continued)

OTHER PUBLICATIONS

O'Neal et al., "Challenges in the packaging of MEMS," Proceedings—International Symposium on Advanced Packaging Materials: Processes, Properties and Interfaces, 22(3), (1999) pp. 41-47. [Online] https://doi.org/10.1109/ISAPM.1999.757284.

(Continued)

*Primary Examiner* — Paul M. West
(74) *Attorney, Agent, or Firm* — Ronald O. Neerings; Frank D. Cimino

(57) ABSTRACT

In examples, a method of manufacturing a fluid sensing package comprises coupling a semiconductor die to a first set of conductive terminals; positioning the semiconductor die within a socket, a fluid probe extending through a probe orifice in a lid of the socket; positioning a ring of the fluid probe on a fluid sensing portion of the semiconductor die by closing the lid of the socket; and using the fluid probe to apply fluid to an area of the fluid sensing portion circumscribed by the ring.

34 Claims, 14 Drawing Sheets

(56) References Cited

U.S. PATENT DOCUMENTS

2015/0316505 A1* 11/2015 Gordon ............ B01L 3/502761
204/601

OTHER PUBLICATIONS

Temiz et al., "Lab-on-a-chip devices: Howto close and plug the lab?" Microelectronic Engineering, 132, (2015) pp. 156-175. [Online] https://doi.org/10.1016/j.mee.2014.10.013.
Oelβner et al., "Encapsulation of ISFET sensor chips," Sensors and Actuators, B: Chemical, 105(1), (2005) pp. 104-117. [Online] https://doi.org/10.1016/j.snb.2004.05.009.

* cited by examiner

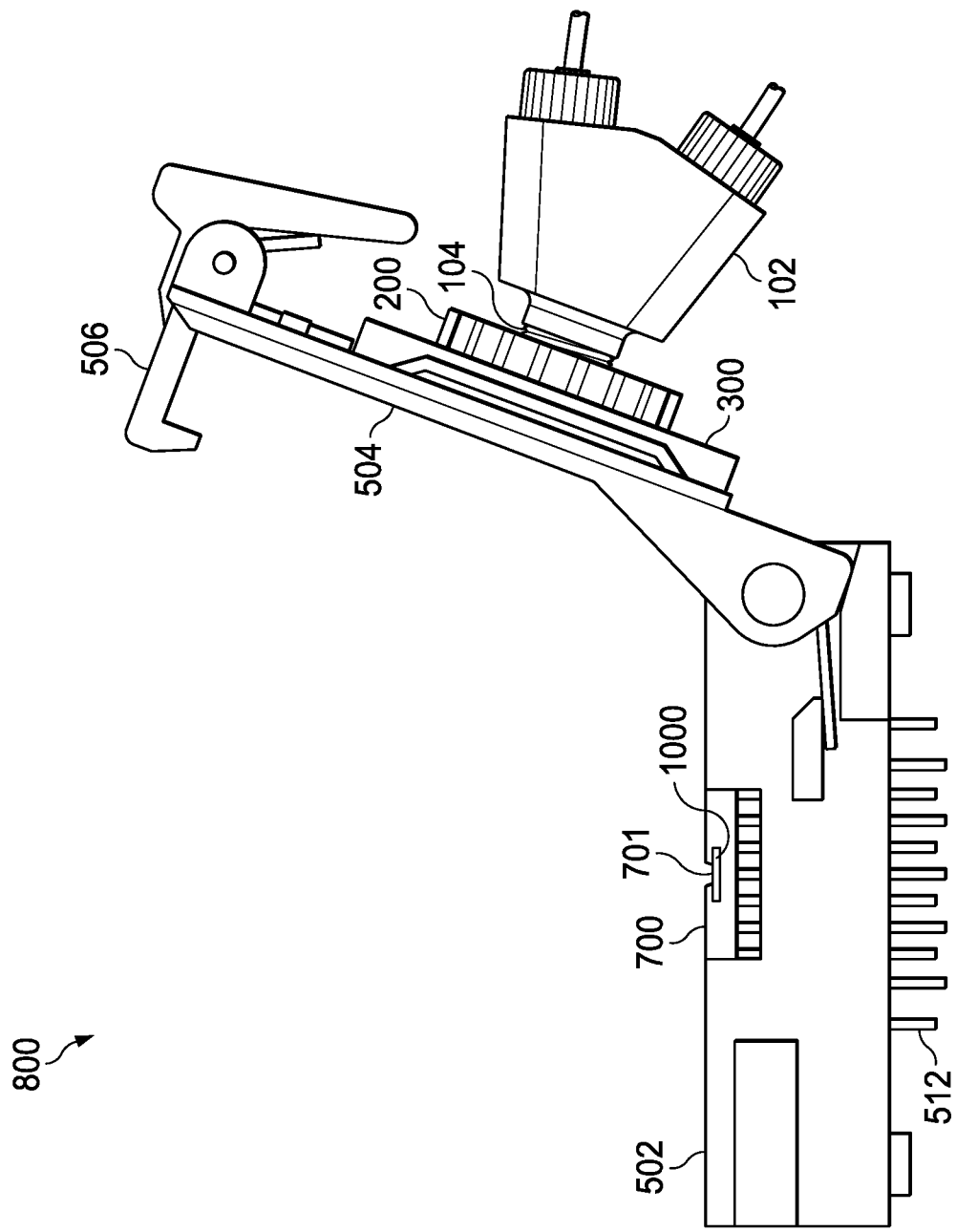

MANUFACTURING FLUID SENSING PACKAGES

CROSS-REFERENCE TO RELATED APPLICATIONS

The present application claims priority to U.S. Provisional Patent Application No. 62/776,236, which was filed Dec. 6, 2018, is titled "METHOD OF FLUIDIC TESTING OF INTEGRATED CIRCUIT SENSOR," and is hereby incorporated herein by reference in its entirety.

SUMMARY

In examples, a method of manufacturing a fluid sensing package comprises coupling a semiconductor die to a first set of conductive terminals; positioning the semiconductor die within a socket, a fluid probe extending through an orifice in a lid of the socket; positioning a ring of the fluid probe on a fluid sensing portion of the semiconductor die by closing the lid of the socket; and using the fluid probe to apply fluid to an area of the fluid sensing portion circumscribed by the ring.

In examples, a system comprises a fluid probe body comprising first and second threaded cavities; a threaded extension coupled to the fluid probe body; a distal fluid inlet extending through the fluid probe body and the threaded extension, the distal fluid inlet meeting the first threaded cavity at an inlet interface; a distal fluid outlet extending through the fluid probe body and the threaded extension, the distal fluid outlet meeting the second threaded cavity at an outlet interface; and a ring coupled to an end of the threaded extension that is distal to the fluid probe body, a fluid inlet orifice of the distal fluid inlet circumscribed by the ring, a fluid outlet orifice of the distal fluid outlet circumscribed by the ring.

BRIEF DESCRIPTION OF THE DRAWINGS

For a detailed description of various examples, reference will now be made to the accompanying drawings in which:

FIG. 8 depicts a side view of a probe and socket assembly, the assembly having a socket with a fluid probe assembly mounted on an opened lid of the socket and a semiconductor die positioned in the socket, in accordance with various examples.

DETAILED DESCRIPTION

Figure 1A:
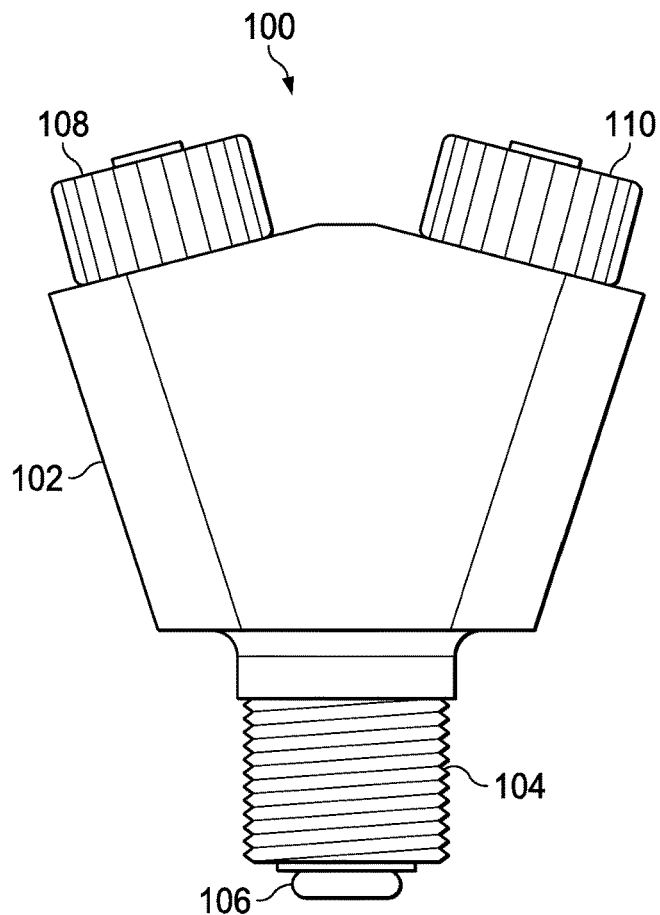
FIG. 1A depicts a front view of a fluid probe, in accordance with various examples.

Electrical circuits are formed on semiconductor dies and subsequently packaged inside moldings (e.g., epoxy) to protect the circuits from damage due to elements external to the package, such as moisture, heat, and blunt force. To facilitate communication with electronics external to the package, an electrical circuit within the package is electrically coupled to conductive terminals. These conductive terminals are positioned inside the package but are exposed to one or more external surfaces of the package. By coupling the conductive terminals to electronics external to the package, a pathway is formed to exchange electrical signals between the electrical circuit within the package and the electronics external to the package via the conductive terminals.

Some types of packages contain semiconductor dies that are configured to measure various properties of fluids. In many instances, the semiconductor die includes a fluid sensing portion that is exposed directly to the fluid to be tested. Thus, for example, a semiconductor die that is configured to measure the various concentrations of chemicals in a swimming pool may be positioned in an area of the pool where the fluid sensing portion of the semiconductor die will be directly exposed to the pool water. These packages are referred to herein as fluid sensing packages.

Fluid sensing packages themselves are tested as part of the package manufacturing process. During such testing, the fluid sensing portion of the die in the fluid sensing package may be exposed to one or more fluid with known properties. Measurements obtained from the fluid sensing package may be compared to the known properties to determine whether the measurements are sufficiently close to the known properties. Fluid sensing packages producing measurements that unsatisfactorily deviate from the known properties may be repaired or discarded.

The process of testing a fluid sensing package is expensive and tedious. In many cases, the fluid sensing package is installed in a water-proof housing so that the fluid does not come in contact with electrically active areas of the die, such as bond pads and bond wires. Such packages may then be tested using an immersion technique. In other cases, a fluid sensing package may have an exposed die that is soldered to a printed circuit board (PCB), and a fluid probe is then manually glued to the exposed die to prevent the fluid from contacting electrically active areas of the die. These testing techniques are tedious, expensive, and inefficient due to the manual performance of at least some of the testing steps. The testing techniques are also undesirably complicated because they involve water-proofing techniques. Moreover, the glue used to connect the fluid probes to the exposed dies is not chemically inert and frequently affect the accuracy of the test results.

This disclosure describes various examples of a method of manufacturing a fluid sensing package. The manufacturing method includes a testing process in which a fluid sensing package (which contains a semiconductor die that is coupled to a first set of conductive terminals, e.g., package leads) is tested to determine whether the die is satisfactory for fluid testing purposes. This testing of the fluid sensing package includes the use of a probe and socket assembly. The socket includes a socket lid which, when opened, reveals a platform and a second set of conductive terminals. The fluid sensing package to be tested is placed on the platform such that the first set of conductive terminals of the fluid sensing package are electrically coupled to the second set of conductive terminals of the socket. The socket lid is then closed and latched. A fluid probe is fixedly mounted on the socket lid and extends through an orifice in the socket lid. An end of the fluid probe that extends through the orifice in the socket lid includes a ring (e.g., a seal ring, a gasket, an o-ring) that, in response to closure of the socket lid, makes contact with a fluid sensing portion of the semiconductor die. The fluid sensing portion of the semiconductor die may be exposed to facilitate direct contact with the ring, and the remainder of the die and other parts of the package may be covered by a molding material, such as epoxy. The fluid probe then applies fluid to an area of the fluid sensing portion circumscribed by the ring, and the fluid probe likewise removes the fluid from the area of the fluid sensing portion circumscribed by the ring. The set of conductive terminals in the socket are electrically coupled to a testing device (e.g., a computer), for example, by way of a printed circuit board (PCB) on which the socket may be mounted. The testing device receives and records signals from the semiconductor die indicating a property of the fluid applied to the semiconductor die. The measured property is compared to an expected property to determine whether the fluid sensing package is operating properly, or if the fluid sensing package is to be repaired or discarded. The manufacturing process may include various other steps that are not expressly described herein.

Figure 9:
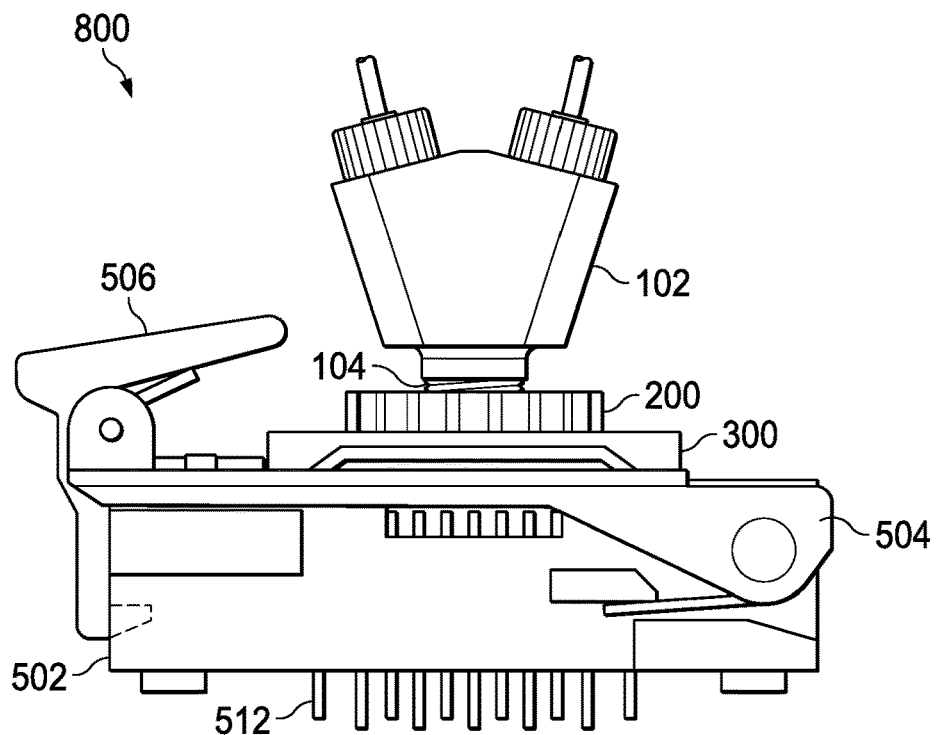
FIG. 9 depicts a side view of a probe and socket assembly, the assembly having a socket with a fluid probe assembly mounted on a closed lid of the socket and a semiconductor die positioned in the socket, in accordance with various examples.
Figure 10:
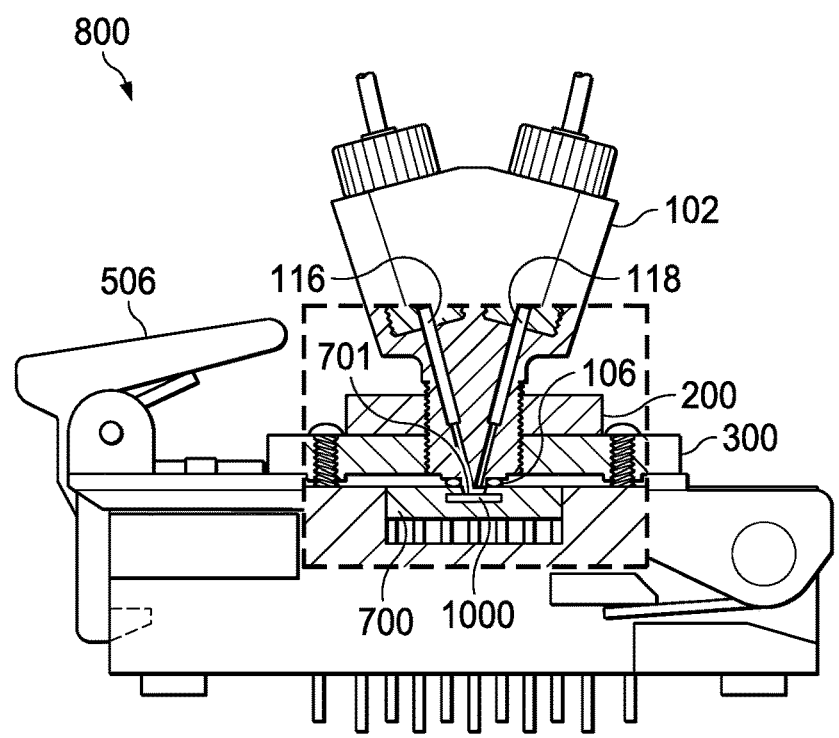
FIG. 10 depicts a partial interior view of a probe and socket assembly, the assembly having a socket with a fluid probe assembly mounted on a closed lid of the socket and a semiconductor die positioned in the socket, in accordance with various examples.
Figure 11:
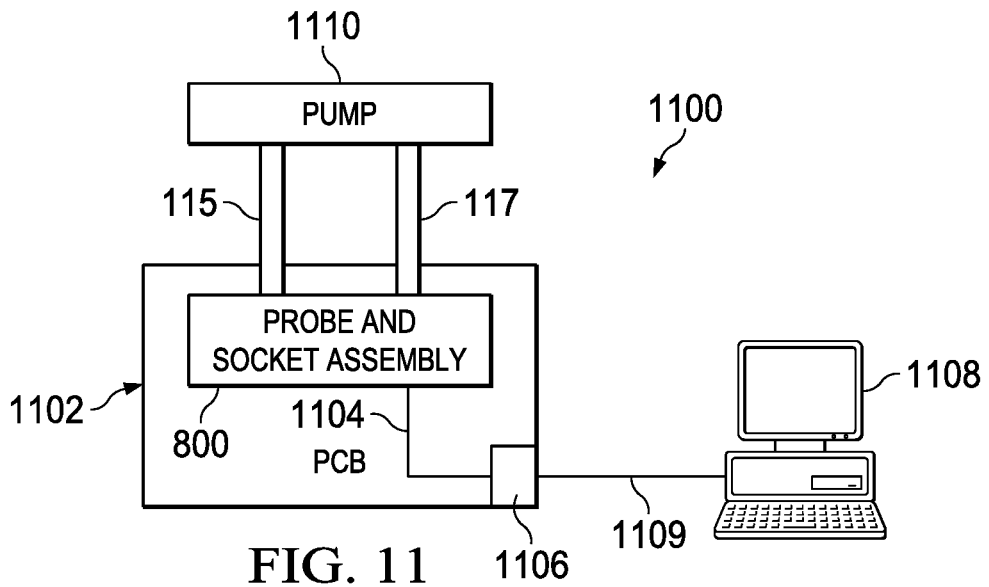
FIG. 11 depicts a schematic block diagram of a test system having a probe and socket assembly, in accordance with various examples.
Figure 12:
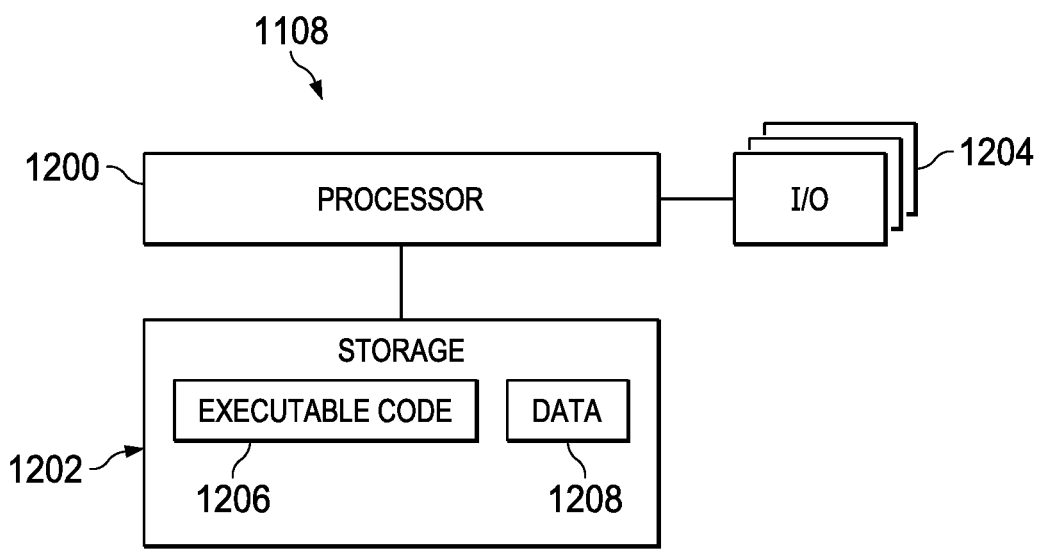
FIG. 12 depicts a schematic block diagram of a testing device of a test system, in accordance with various examples.
Figure 13:
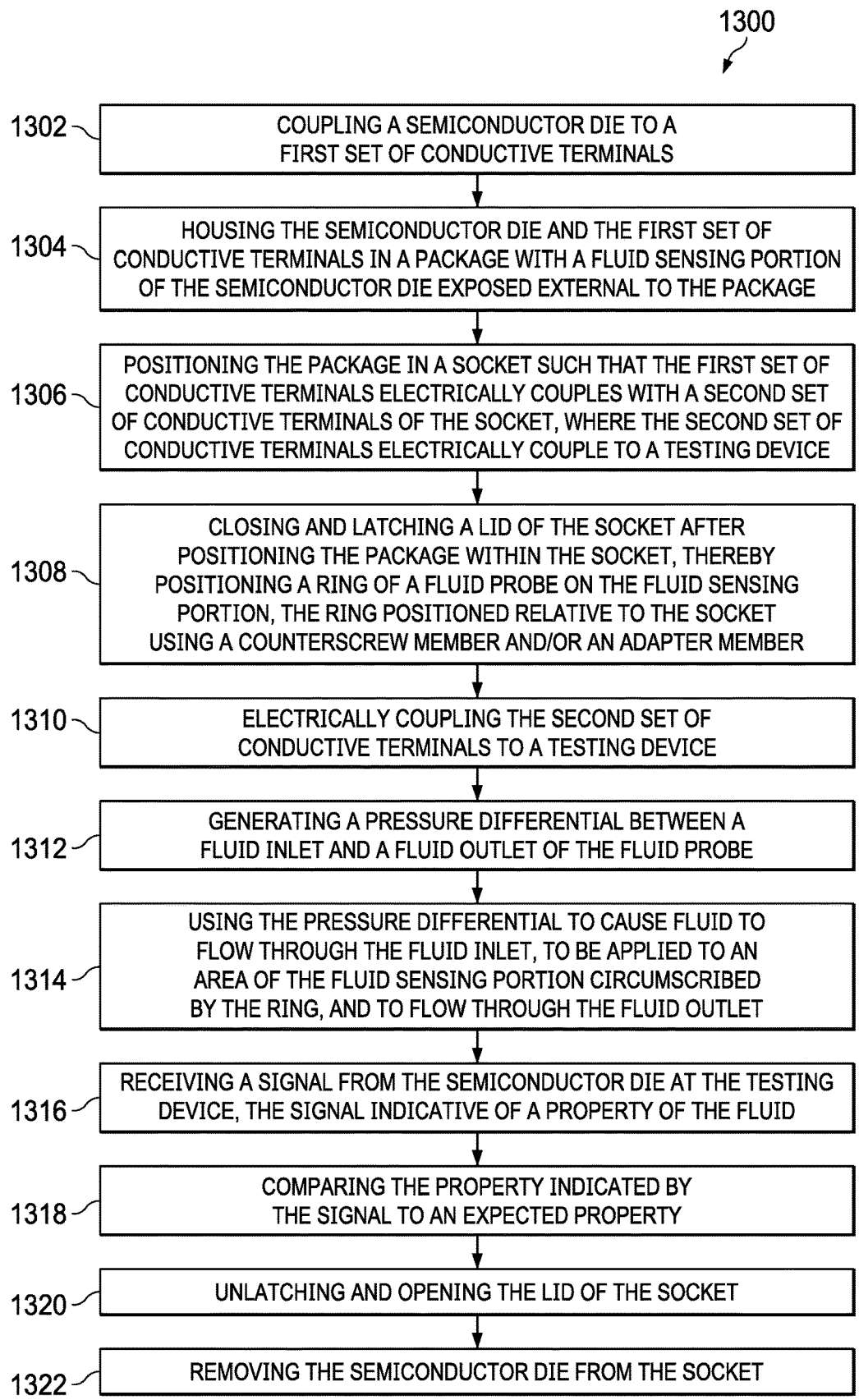
FIG. 13 depicts a flow diagram of a method of manufacturing a fluid sensing package, in accordance with various examples.

The probe and socket assembly mentioned above includes a fluid probe that is fixedly mounted on a socket, as explained. FIGS. 1A-4D depict the fluid probe, FIGS. 5A-7B depict the socket, FIGS. 8-10 depict the probe and socket assembly, FIGS. 11 and 12 depict aspects of the test system used to manufacture fluid sensing packages using the probe and socket assembly, and FIG. 13 depicts a method of manufacturing the fluid sensing packages using aspects of the test system. Each of these drawings is now described in turn.

FIG. 1A depicts a front view of a fluid probe 100, in accordance with various examples. The fluid probe 100 may include a main body 102, a threaded extension 104, a ring 106 (e.g., a seal ring, a gasket, an o-ring), a fluid inlet member 108, and a fluid outlet member 110. The main body 102 is depicted as being of a pentagonal shape in the front view of FIG. 1A, although the scope of this disclosure is not limited to any particular shape or size of the main body 102. The threaded extension 104 is threaded such that other threaded items, such as the members depicted in FIGS. 2A-3C, may be fastened to the threaded extension 104 by rotating the members relative to the threaded extension 104 (or vice versa). The ring 106 is positioned on a distal end of the threaded extension 104. In some examples, the ring 106 is composed of rubber, although other materials suitable for forming waterproof and airtight seals also may be used. In examples, the diameter of the ring 106 is less than or equal to the diameter of the threaded extension 104.

FIG. 1A depicts only a portion of the fluid inlet member 108, as the remainder of the fluid inlet member 108 is positioned inside a cavity of the main body 102. As described below, the portion of the fluid inlet member 108 positioned inside the main body 102 includes a fluid inlet (e.g., tube) that interfaces with another fluid inlet (e.g., tube) that is part of the main body 102 and that leads through the threaded extension 104 and out the ring 106.

Similarly, FIG. 1A depicts only a portion of the fluid outlet member 110, as the remainder of the fluid outlet member 110 is positioned inside a cavity of the main body 102. As described below, the portion of the fluid outlet member 110 positioned inside the main body 102 includes a fluid outlet (e.g., tube) that interfaces with another fluid outlet (e.g., tube) that is part of the main body 102 and that leads from the ring 106, through the threaded extension 104, and into the main body 102. The portion of the fluid inlet member 108 inside the main body 102 may be threaded, and the corresponding cavity may be threaded in a complementary manner to facilitate screwing of the fluid inlet member 108 into the cavity. The fluid outlet member 110 and its associated cavity may be similarly threaded. In examples, grooves are formed in the portions of the fluid inlet member 108 and the fluid outlet member 110 that are visible in FIG. 1A, thus enhancing finger grip on those portions and facilitating the aforementioned screwing. In examples, at least some of the fluid probe 100 (e.g., the main body 102, the threaded extension 104) is composed at least in part of polyetheretherketone (PEEK) or another suitable material.

Figure 1B:
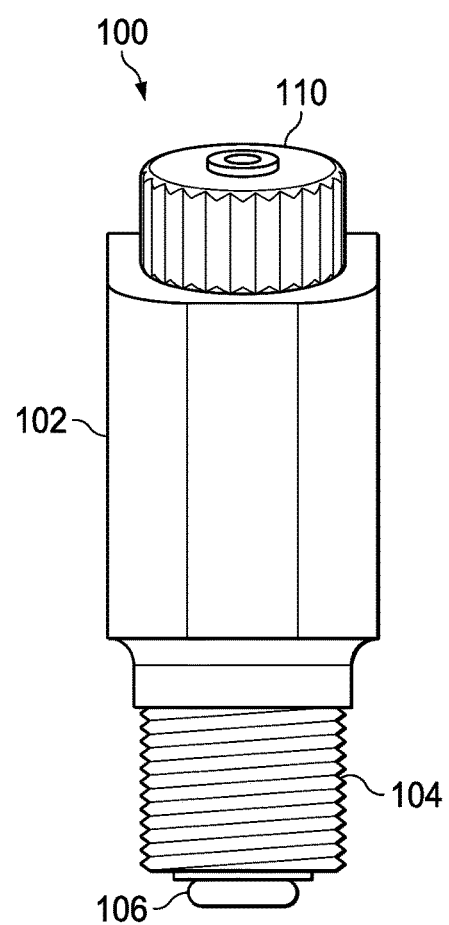
FIG. 1B depicts a side view of a fluid probe, in accordance with various examples.
Figure 1C:
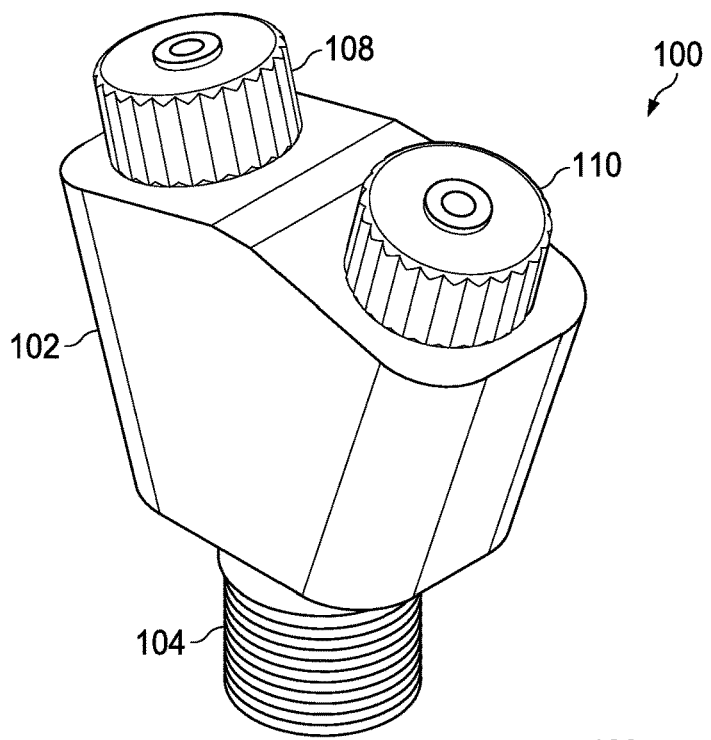
FIG. 1C depicts a perspective view of a fluid probe, in accordance with various examples.

FIG. 1B depicts a side view of the fluid probe 100, in accordance with various examples. FIG. 1C depicts a perspective view of the fluid probe 100, in accordance with various examples. As mentioned above, the shape and size of the fluid probe 100 is merely illustrative and non-limiting.

Figure 1D:
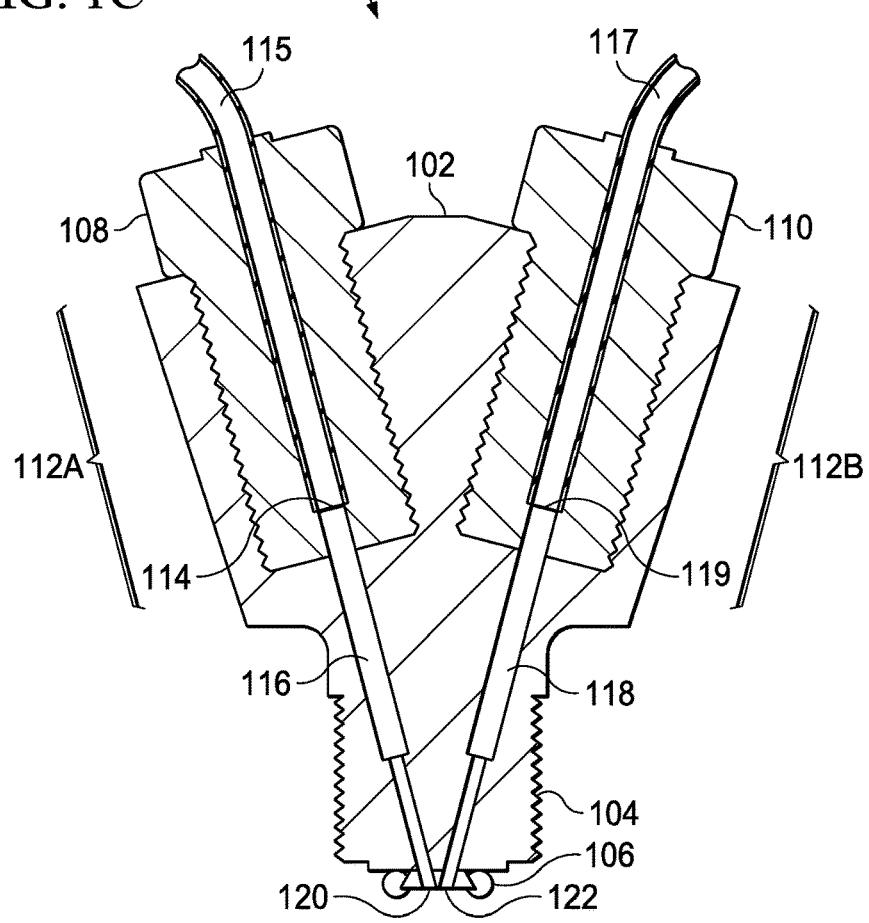
FIG. 1D depicts a cross-sectional front view of a fluid probe, in accordance with various examples.

FIG. 1D depicts a cross-sectional front view of the fluid probe 100, in accordance with various examples. The main body 102 may include two threaded cavities 112A and 112B, such as those mentioned above. The threaded cavity 112A may be referred to herein as the "first threaded cavity" and the threaded cavity 112B may be referred to herein as the "second threaded cavity." The fluid inlet member 108 is threaded and is screwed into the threaded cavity 112A, and the fluid outlet member 110 is threaded and is screwed into the threaded cavity 112B. As shown, the fluid inlet member 108 houses a proximal fluid inlet 115, and the fluid outlet member 110 houses a proximal fluid outlet 117. The main body 102 includes a distal fluid inlet 116 that interfaces with the proximal fluid inlet 115 at the distal end of the fluid inlet member 108. Numeral 114 marks this inlet interface. An optional seal (e.g., rubber seal), which is not expressly shown, may be positioned at this inlet interface 114 to mitigate leakage of fluid into the threaded cavity 112A. The main body 102 includes a distal fluid outlet 118 that interfaces with the proximal fluid outlet 117 at the distal end of the fluid outlet member 110. Numeral 119 marks this outlet interface. An optional seal (e.g., rubber seal), which is not expressly shown, may be positioned at this outlet interface 119 to mitigate leakage of fluid into the threaded cavity 112B. The distal fluid inlet 116 and the distal fluid outlet 118 are positioned at an angle with respect to each other such that they converge at the ring 106. The distal fluid inlet 116 includes a fluid inlet orifice 120, and the distal fluid outlet 118 includes a fluid outlet orifice 122. The orifices 120, 122 are positioned within the diameter of the ring 106, as shown. In examples, the ring extends more distally from the main body 102 than do the distal fluid inlet 116 and distal fluid outlet 118. The shape and general design of the distal fluid inlet 116 and distal fluid outlet 118 may be modified as desired.

Figure 1E:
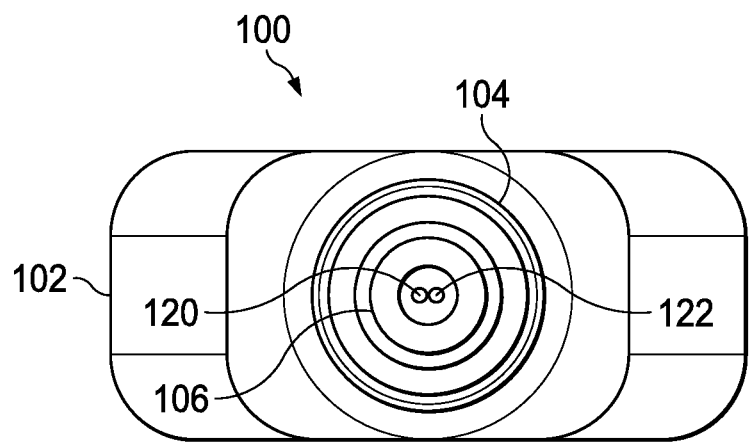
FIG. 1E depicts a bottom-up view of a seal ring of a fluid probe and fluid inlet and outlet orifices of the fluid probe, in accordance with various examples.

FIG. 1E depicts a bottom-up view of the seal ring 106 of the fluid probe 100. As shown, the orifices 120 and 122 are positioned within the diameter of the ring 106, with the fluid inlet orifice 120 terminating the distal fluid inlet 116 and the fluid outlet orifice 122 originating the distal fluid outlet 118. FIG. 1E does not depict portions of the fluid probe 100 that appear outside the diameter of the ring 106 in a bottom-up view.

The operation of the fluid probe 100 may be most conveniently described with respect to FIG. 1D. Referring to FIG. 1D, fluid is pumped into the proximal fluid inlet 115, which, in turn, conveys the fluid to the distal fluid inlet 116. The fluid exits the distal fluid inlet 116 at the fluid inlet orifice 120 and is applied to a fluid sensing portion of a semiconductor die being tested during manufacture of a fluid sensing package. The fluid is prevented from contacting electrically active areas of the fluid sensing package by the ring 106, which may form a waterproof and airtight seal with the fluid sensing portion of the semiconductor die, or with another suitable portion of the semiconductor die. Areas outside the ring 106 are protected from fluid contact by the ring 106 and/or by molding material of the fluid sensing package that covers those areas. Because there exists a pressure differential between the fluid inlets and the fluid outlets (e.g., generated by a pump that pumps the fluid into the proximal fluid inlet 115), the fluid is removed from the fluid sensing portion of the semiconductor die via the orifice fluid outlet 122, the distal fluid outlet 118, and the proximal fluid outlet 117. Measurements of one or more fluid parameters are made using the semiconductor die, and these measurements are communicated to a testing device (e.g., a computer), where they are subsequently compared to expected measurements to determine whether the fluid sensing package is performing adequately or whether the fluid sensing package requires repair (or to be discarded).

Figure 2A:
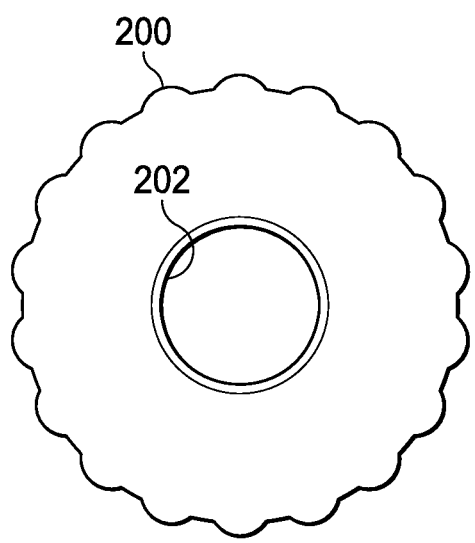
FIG. 2A depicts a top-down view of a counterscrew member, in accordance with various examples.
Figure 2B:
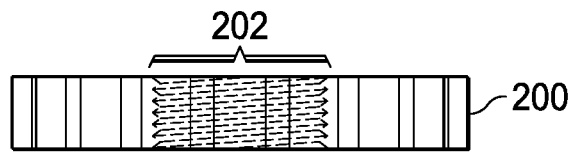
FIG. 2B depicts a side view of a counterscrew member, in accordance with various examples.

FIG. 2A depicts a top-down view of a counterscrew member 200, in accordance with various examples. In examples, the counterscrew member 200 is circular in shape in the top-down view. In examples, the counterscrew member 200 includes a threaded counterscrew orifice 202 which may be used to fasten the counterscrew member 200 to the threaded extension 104. In examples, the counterscrew member 200 is composed of PEEK, although other materials may be used. FIG. 2B depicts a side view of the counterscrew member 200, in accordance with various examples. The threaded counterscrew orifice 202 is depicted by dashed lines, as shown. As FIG. 2B depicts, an exterior surface along the circumference of the counterscrew member 200 may be ridged (or "grooved") to improve handgrip.

Figure 3A:
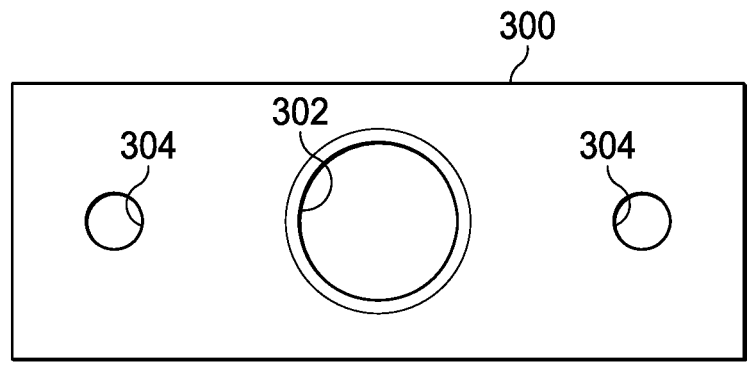
FIG. 3A depicts a top-down view of an adapter member, in accordance with various examples.

FIG. 3A depicts a top-down view of an adapter member 300, in accordance with various examples. The adapter member 300 is rectangular in shape in the top-down view. In examples, the adapter member 300 includes a threaded extension orifice 302 which may be used to fasten the adapter member 300 to the threaded extension 104. In examples, the adapter member 300 includes threaded socket orifices 304 that are usable to fasten the adapter member 300 to a socket in the probe and socket assembly (e.g., using screws), as described below. Because the adapter member 300 may be fastened to the socket, and because the adapter member 300 may be fastened to the fluid probe 100, which, in turn, is fastened to the counterscrew member 200, the entire fluid probe assembly (including the fluid probe 100, counterscrew member 200, and adapter member 300) is fastened (or "mounted") to the socket. Other techniques may be used to fasten the various components of the fluid probe assembly.

Figure 3B:
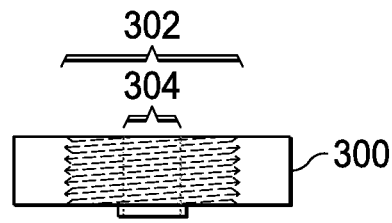
FIG. 3B depicts an end view of an adapter member, in accordance with various examples.
Figure 3C:
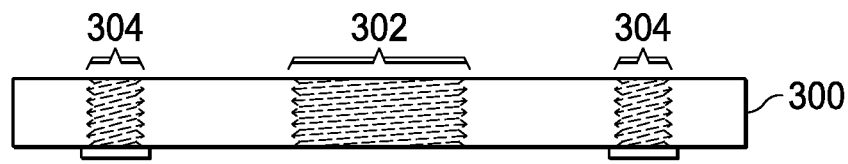
FIG. 3C depicts a side view of an adapter member, in accordance with various examples.

FIG. 3B depicts an end view of the adapter member 300, in accordance with various examples. The threaded orifices 302, 304 are depicted by dashed lines, as shown. FIG. 3C depicts a side view of the adapter member 300, in accordance with various examples. The threaded orifices 302, 304 are depicted by dashed lines, as shown.

Figure 4A:
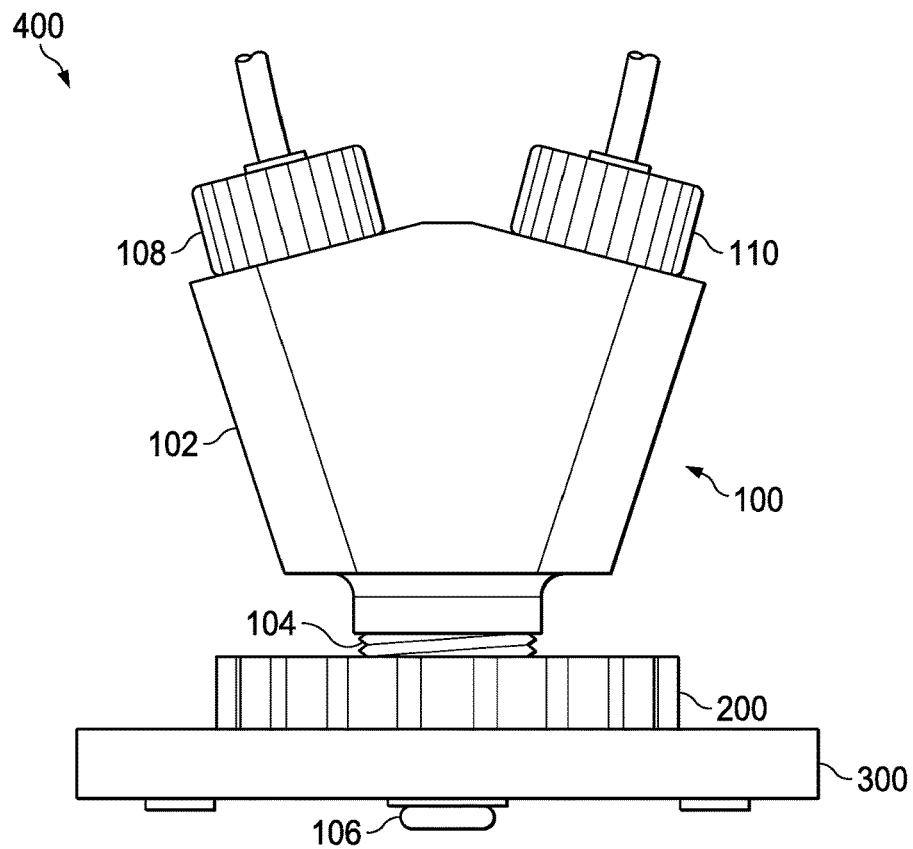
FIG. 4A depicts a front view of a fluid probe assembly comprising a fluid probe coupled to a counterscrew member and an adapter member, in accordance with various examples.

FIG. 4A depicts a front view of a fluid probe assembly 400 comprising a fluid probe 100 coupled to a counterscrew member 200 and an adapter member 300, in accordance with various examples. As explained, the counterscrew member 200 contains a threaded orifice (e.g., threaded counterscrew orifice 202 in FIG. 2A) that may be used to fasten the counterscrew member 200 to the threaded extension 104. Similarly, as explained, the adapter member 300 contains a threaded orifice (e.g., threaded extension orifice 302 in FIG. 3A) that may be used to fasten the adapter member 300 to the threaded extension 104. The positions of the counterscrew member 200 and the adapter member 300 on the threaded extension 104 may be raised or lowered as desired. In some examples, the distance between the counterscrew member 200 and the adapter member 300 may be increased relative to that shown in FIG. 4A and in other examples this distance may be decreased. The counterscrew member 200 and the adapter member 300 generally function to fix a predetermined position of the fluid probe 100 (and, more particularly, of the ring 106) relative to the socket, which is described in detail below. Specifically, the adapter member 300 fastens the fluid probe 100 to the socket, and the counterscrew member 200 limits the degree to which the fluid probe 100 can extend through the lid of the socket.

Figure 4B:
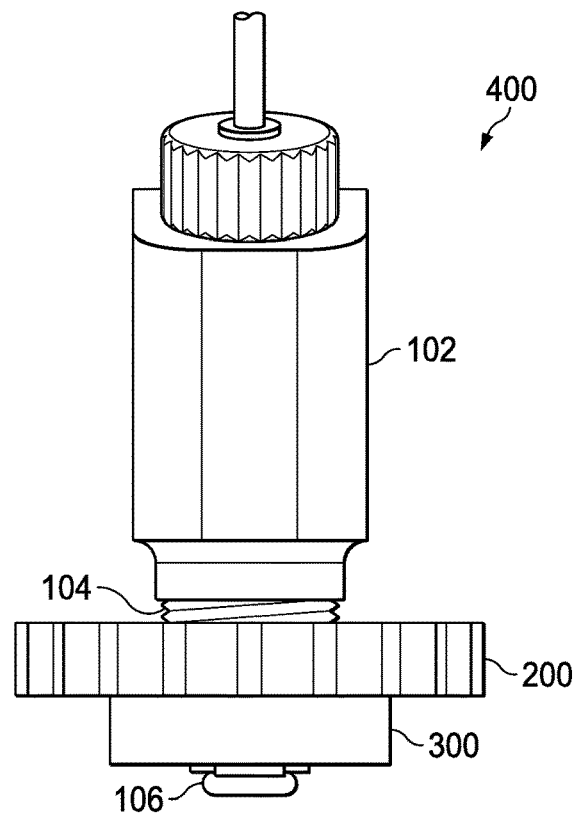
FIG. 4B depicts a side view of a fluid probe assembly comprising a fluid probe coupled to a counterscrew member and an adapter member, in accordance with various examples.
Figure 4C:
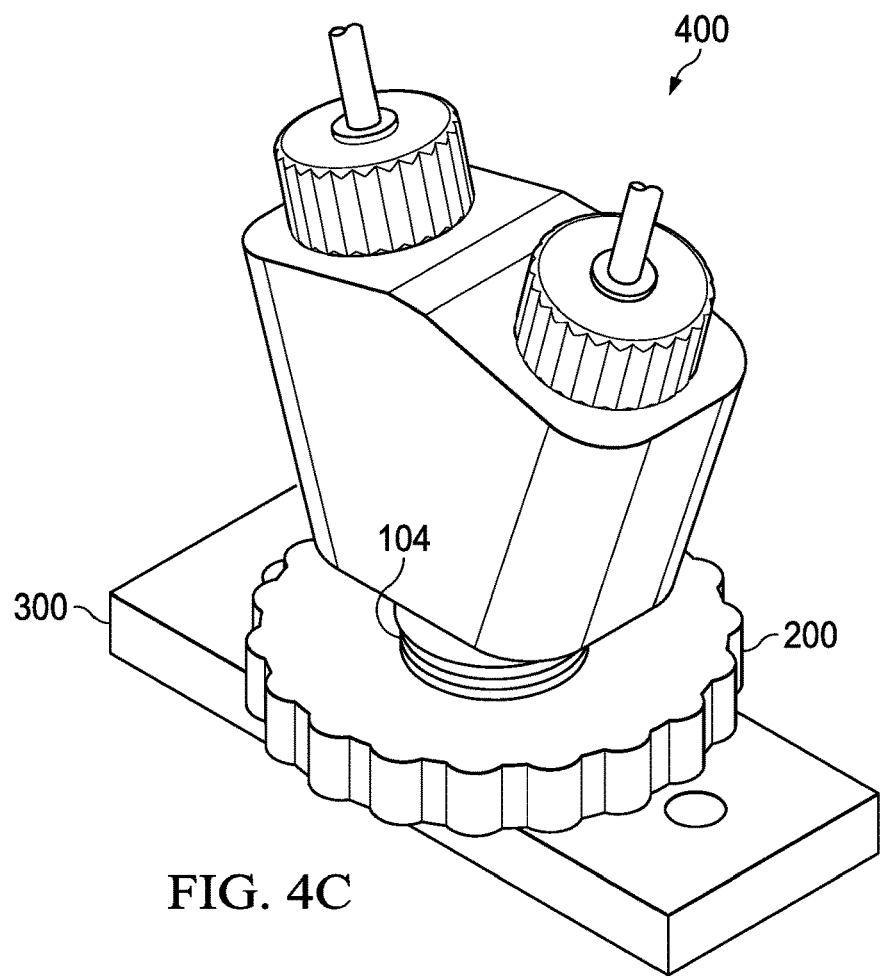
FIG. 4C depicts a perspective view of a fluid probe assembly comprising a fluid probe coupled to a counterscrew member and an adapter member, in accordance with various examples.
Figure 4D:
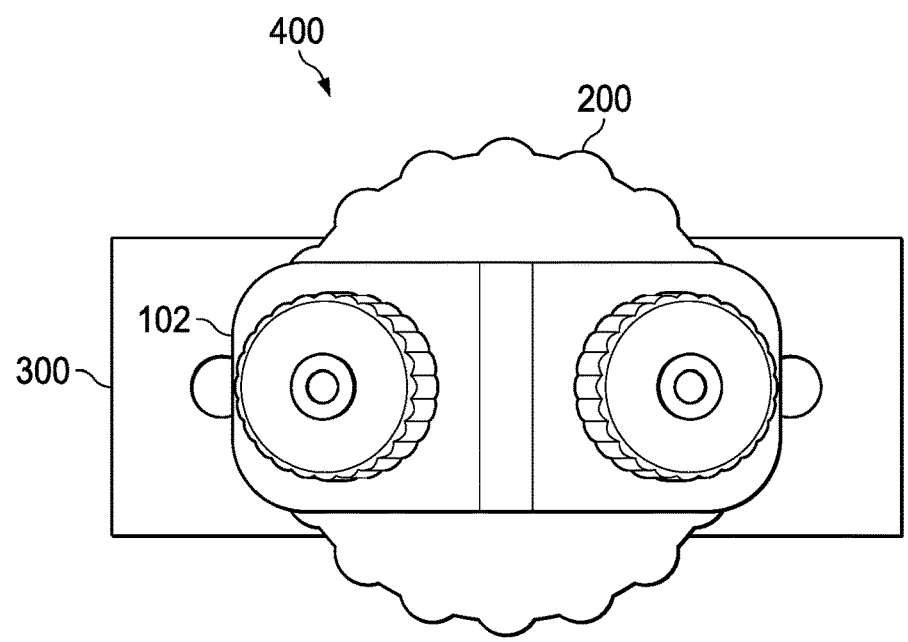
FIG. 4D depicts a top-down view of a fluid probe assembly comprising a fluid probe coupled to a counterscrew member and an adapter member, in accordance with various examples.

FIG. 4B depicts a side view of the fluid probe assembly 400, in accordance with various examples. FIG. 4C depicts a perspective view of the fluid probe assembly 400, in accordance with various examples. FIG. 4D depicts a top-down view of the fluid probe assembly 400, in accordance with various examples.

Figure 5A:
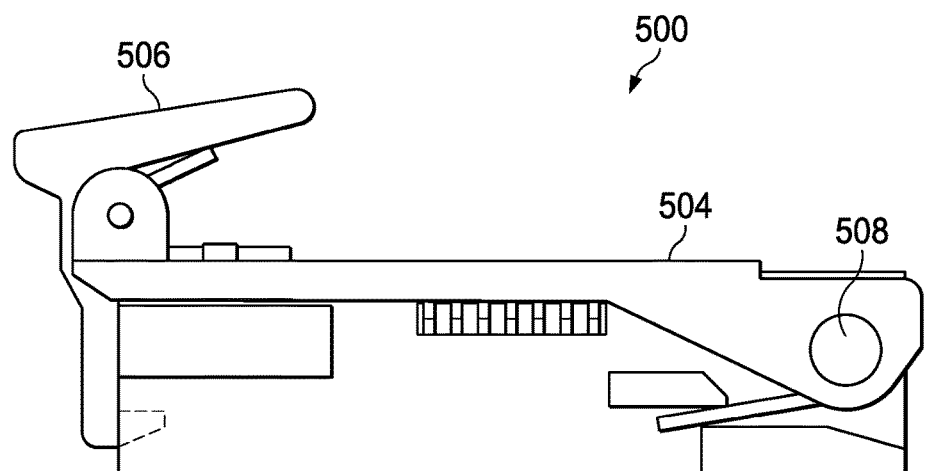
FIG. 5A depicts a side view of a socket with a closed lid, in accordance with various examples.
Figure 5B:
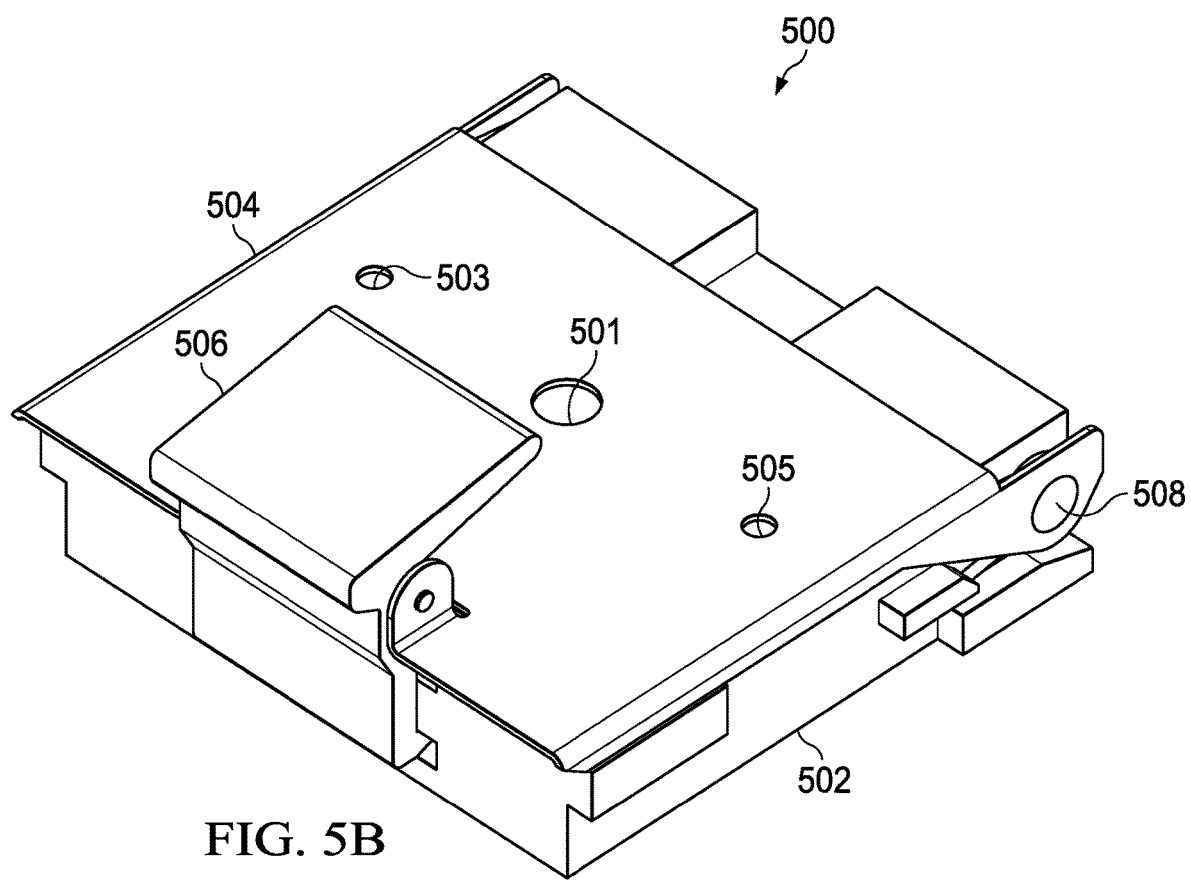
FIG. 5B depicts a perspective view of a socket with a closed lid, in accordance with various examples.

As explained above, a probe and socket assembly comprises a fluid probe assembly, which is described above, and a socket, which is now described. FIG. 5A depicts a side view of a socket 500, in accordance with various examples. The socket 500 as depicted in FIG. 5A has a socket body 502, a socket lid 504 (also referred to herein as a "lid of the socket"), a latch mechanism 506, and a hinge 508. As shown in FIG. 5B, the socket lid 504 includes a probe orifice 501 and screw orifices 503, 505. The probe orifice 501 is configured to allow the threaded extension 104 and/or the ring 106 of the fluid probe 100 (e.g., FIG. 1D) to pass therethrough. The screw orifices 503, 505 are configured to receive fastening members, such as screws, that pass through the threaded socket orifices 304 of the adapter member 300 (e.g., FIG. 3A) to fasten the adapter member 300 to the socket lid 504. Thus, using the orifices 501, 503, and 505, the fluid probe assembly 400 (e.g., FIG. 4A) may be mounted to the socket 500, and more specifically to the socket lid 504.

The socket lid 504 is rotatable about the hinge 508, thus permitting the socket lid 504 to open and close. The socket lid 504 may be opened so that a semiconductor die (either packaged or not packaged) may be positioned inside the socket 500. The socket lid 504 may then be closed and the latch mechanism 506 engaged to lock the socket lid 504 shut. The socket lid 504 may be opened and closed with the fluid probe assembly 400 mounted on the socket lid 504. FIGS. 8-10 depict this configuration in greater detail and are described below. FIG. 5B depicts a perspective view of the socket 500 with a closed socket lid 504, in accordance with various examples.

Figure 6A:
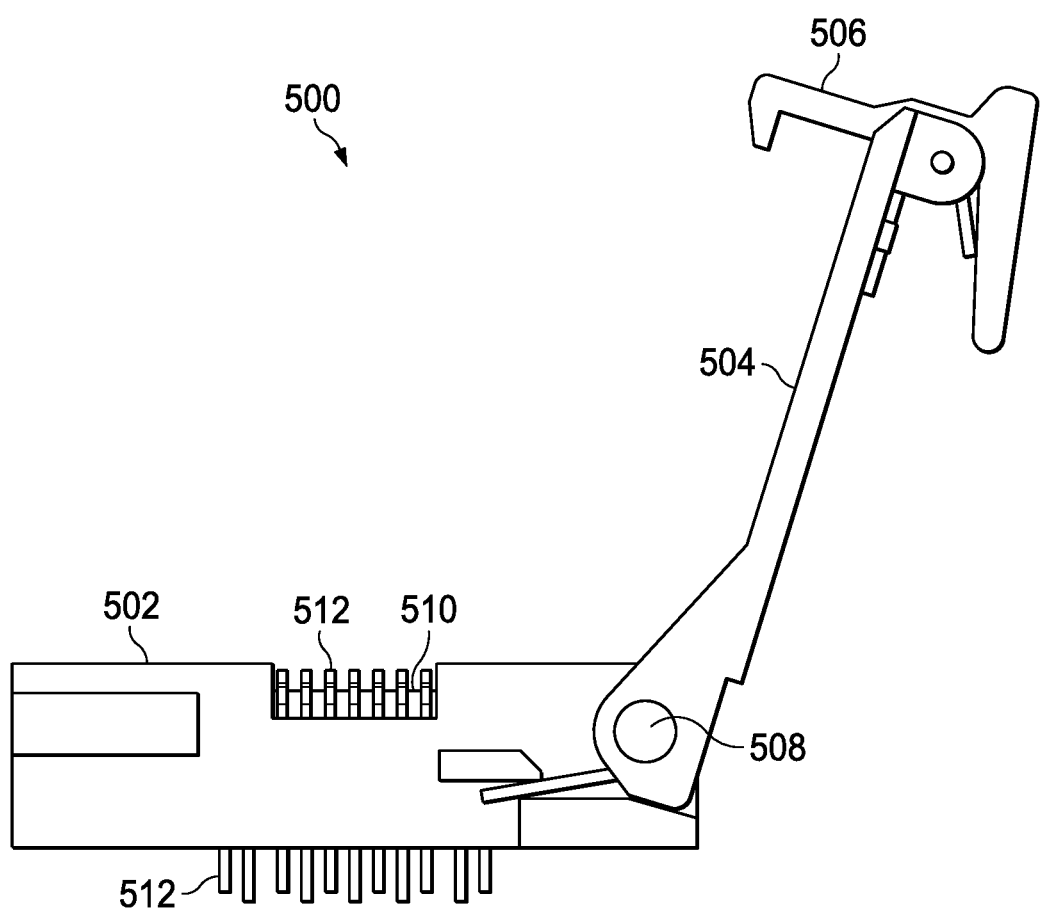
FIG. 6A depicts a side view of a socket with an opened lid, in accordance with various examples.
Figure 6B:
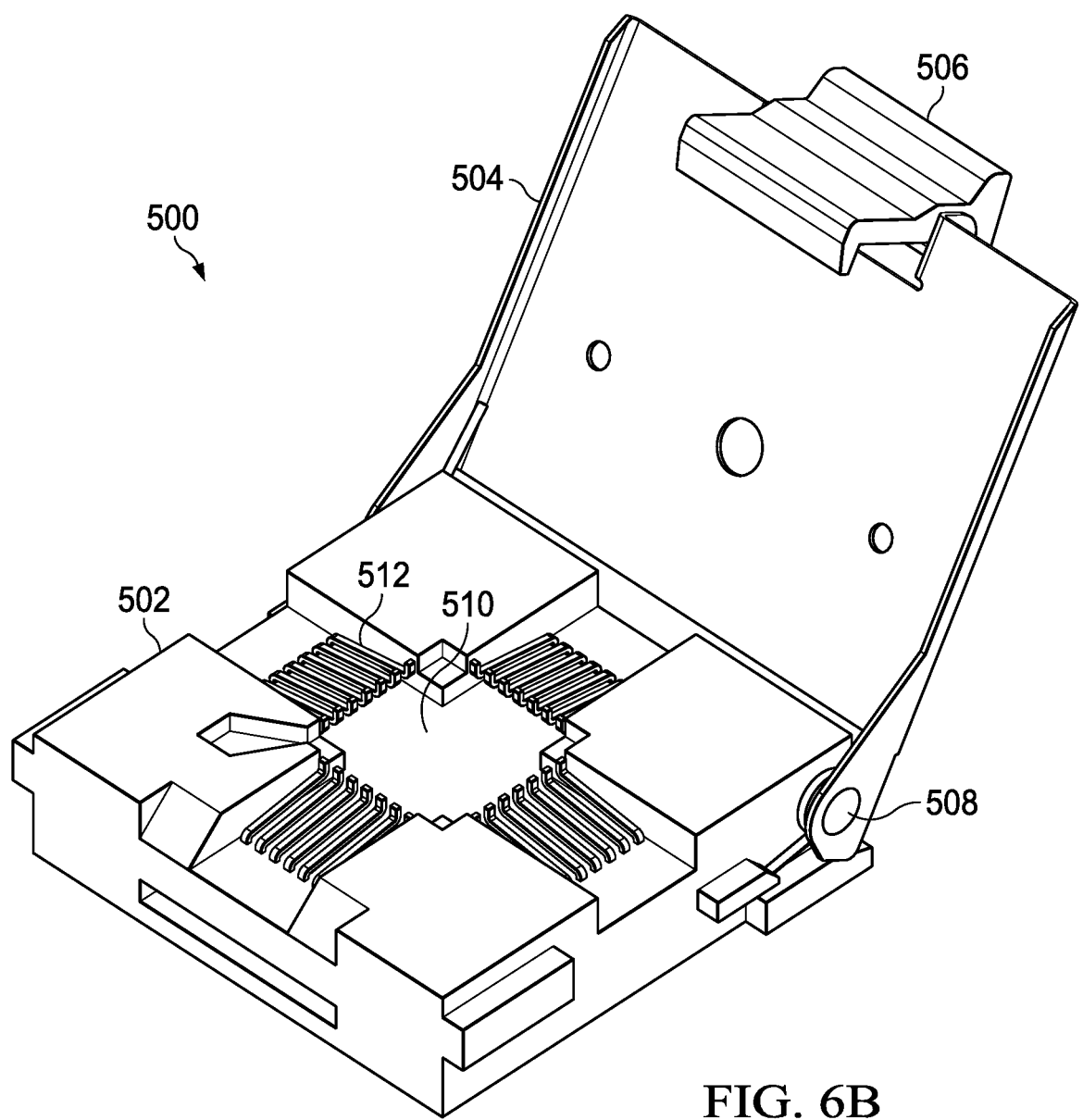
FIG. 6B depicts a perspective view of a socket with an opened lid, in accordance with various examples.

FIG. 6A depicts a side view of the socket 500 with an opened socket lid 504, in accordance with various examples. A platform 510 is formed in the socket body 502 and a set of conductive terminals 512 (also referred to herein as a second set of conductive terminals 512) is positioned along a perimeter of the platform 510. In some examples, the platform 510 is positioned in the center of a top surface of the socket body 502. The set of conductive terminals 512 surrounding the platform 510 are positioned such that the conductive terminals of a fluid sensing package mounted on the platform 510 would be in contact with the set of conductive terminals 512. The conductive terminals 512 extend through the socket body 502 and extend through a bottom surface of the socket body 502, as shown. The pattern of conductive terminals 512 on the top side of the socket body 502 may differ from the pattern of conductive terminals 512 on the bottom side of the socket body 502 due to the different components to which each side couples. The conductive terminals 512 on the top side of the socket body 502 couple to package leads, whereas the conductive terminals 512 on the bottom side of the socket body 502 couple to, e.g., a PCB. The portions of the conductive terminals 512 that extend through the bottom surface of the socket body 502 may be coupled to electrical terminals on a PCB, for example. FIG. 6B depicts a perspective view of the socket 500 with the opened socket lid 504.

Figure 7A:
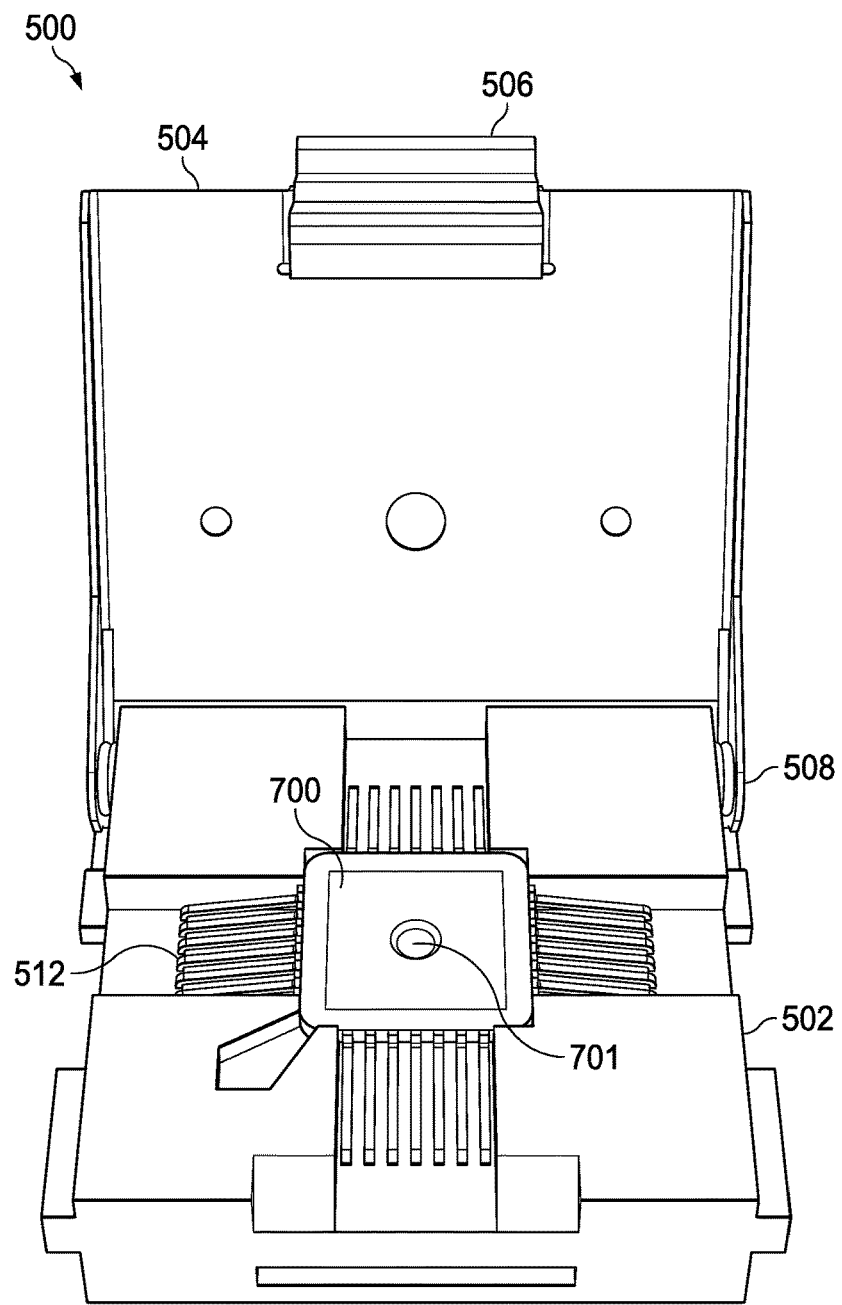
FIG. 7A depicts another perspective view of a socket with an opened lid and a semiconductor die positioned in the socket, in accordance with various examples.
Figure 7B:
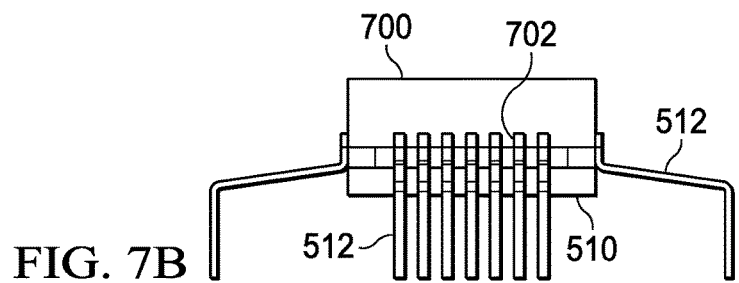
FIG. 7B depicts a front view of a portion of a socket with a semiconductor die positioned in the socket, in accordance with various examples.

FIG. 7A depicts a perspective view of the socket 500 with an opened socket lid 504 and a fluid sensing package 700 positioned on the platform 510 (shown in, e.g., FIGS. 6A and 6B), in accordance with various examples. As shown, the fluid sensing package 700 includes molding material that covers substantially all portions of the semiconductor die, except for an exposed fluid sensing portion 701 of the fluid sensing package 700. When the fluid sensing package 700 is mounted as shown, the conductive terminals (not visible in the view of FIG. 7A, but shown in FIG. 7B) of the fluid sensing package 700 couple to the conductive terminals 512 of the socket 500. (In some examples, the conductive terminals 512 couple to springs coupled to the socket 500 that render the conductive terminals 512 sufficiently mobile to facilitate coupling to the fluid sensing package 700 in cases where portions of the socket 500 or the fluid sensing package 700 are uneven.) When the open socket lid 504 is closed and the latch mechanism 506 is engaged, additional force is applied to the top of the fluid sensing package 700, thus causing the conductive terminals 702 of the fluid sensing package 700 to firmly and securely contact the conductive terminals 512. Because of the flexibility of the ring 106 (e.g., FIG. 1D) and the optional springs of the socket 500 described above, fastening members positioned in the threaded socket orifices 304 (e.g., FIG. 3A) control the force with which the seal between the ring 106 and the fluid sensing portion 701 is generated. FIG. 7B depicts a front view of a portion of the socket 500 with the fluid sensing package 700 positioned in the socket 500, in accordance with various examples. As shown, conductive terminals 702 of the fluid sensing package 700 (e.g., the terminals in a quad flat no-leads package, the leads of a leaded package) make contact with the set of conductive terminals 512 of the socket 500. The conductive terminals 702 may be referred to herein as the "first set of conductive terminals," and the conductive terminals 512 may be referred to herein as the "second set of conductive terminals."

FIG. 8 depicts a side view of a probe and socket assembly 800, in accordance with various examples. The probe and socket assembly 800 includes a fluid probe assembly (such as fluid probe assembly 400 of FIG. 4A) mounted on an opened socket lid 504 and a fluid sensing package 700 positioned in the socket body 502, as shown. The fluid sensing package 700 houses a semiconductor die 1000, which includes an exposed fluid sensing portion 701. As explained above, the adapter member 300 couples to the socket lid 504 using fastening members, such as screws, and the fluid probe main body 102 couples to the adapter member 300 (and, optionally, the counterscrew member 200) using the threaded extension 104. In addition, the set of conductive terminals 702 (e.g., FIG. 7B) of the fluid sensing package 700, when positioned in the socket body 502, couple to the set of conductive terminals 512 of the socket body 502 (e.g., FIG. 6A). The conductive terminals 512 extend through the bottom surface of the socket body 502, as shown, so that they may electrically couple to a testing device (e.g., via a PCB).

FIG. 9 depicts a side view of the probe and socket assembly 800, in accordance with various examples. In FIG. 9, the socket lid 504 is closed, and the latch mechanism 506 is engaged. When the latch mechanism 506 is engaged, the socket lid 504 presses on the top of the fluid sensing package 700 (e.g., FIG. 8), thereby promoting a firm coupling of the conductive terminals of the fluid sensing package 700 and the socket body 502.

FIG. 10 depicts a partial interior view of the probe and socket assembly 800, in accordance with various examples. As shown, when the socket lid 504 is closed and the latch mechanism 506 is engaged, the ring 106 presses firmly against a fluid sensing portion 701 of the semiconductor die 1000, thereby forming a waterproof and airtight seal. Fluid is applied to the fluid sensing portion 701 via the distal fluid inlet 116 and is removed from the fluid sensing portion 701 via the distal fluid outlet 118. The semiconductor die 1000 provides electrical signals indicating information about the sensed fluid to the conductive terminals 512, which, in turn, provide the electrical signals to a testing device (e.g., a computer) for analysis.

FIG. 11 depicts a schematic block diagram of a test system 1100, in accordance with various examples. The test system 1100 includes a probe and socket assembly 800 mounted on a PCB 1102. The PCB 1102 includes a metal trace 1104 that couples the probe and socket assembly 800 to an interface 1106. The interface 1106 couples the metal trace 1104 to a testing device 1108 (e.g., a computer) via a connection 1109. In addition, the probe and socket assembly 800 includes a proximal fluid inlet 115 and a proximal fluid outlet 117 that couple to a fluid pump 1110. The fluid pump 1110 provides fluid to the probe and socket assembly 800 via the proximal fluid inlet 115, and the probe and socket assembly 800 applies the fluid to the fluid sensing portion of a semiconductor die, as explained in detail above. Because the fluid pump 1110 generates a pressure differential between the proximal fluid inlet 115 and the proximal fluid outlet 117, the fluid is removed from the semiconductor die and returned to the fluid pump 1110 via the proximal fluid outlet 117. The probe and socket assembly 800 provides signals to the testing device 1108 that include information about the fluid gathered by the semiconductor die. The information may include, for example, one or more properties of the fluid. The testing device 1108 then analyzes the information, for example, by comparing the measured fluid properties to expected fluid properties to determine whether the semiconductor die is operating properly. If the measured fluid properties are within an acceptable range of the expected fluid properties, the testing device 1108 may provide a signal (e.g., on a display) indicating that the semiconductor die passed the test. Otherwise, the testing device 1108 may provide a signal indicating that the semiconductor die did not pass the test. Once a semiconductor die has been tested, the socket lid 504 (e.g., FIG. 5A) in the probe and socket assembly 800 may be opened, the semiconductor die may be removed, a new semiconductor die may be placed in the socket body 502 (e.g., FIG. 5A), and the socket lid 504 may be closed to begin another test. In some examples, some or all of the aforementioned actions may be performed by a machine, such as an automated pick-and-place machine, to improve testing efficiency.

FIG. 12 depicts a schematic block diagram of a testing device 1108 of a test system 1100 (e.g., FIG. 11), in accordance with various examples. The testing device 1108 may comprise a processor 1200 coupled to storage 1202 and input/output device(s) 1204 (e.g., displays, keyboards, touchscreens, mice). The storage 1202 comprises executable code 1206, which, when executed by the processor 1200, causes the processor 1200 to perform some or all of the actions attributed in this disclosure to testing devices. The storage 1202 also may comprise data 1208, such as expected fluid property values against which measured fluid property values may be compared.

FIG. 13 depicts a flow diagram of a method of manufacturing a fluid sensing package 1300, in accordance with various examples. The method 1300 may comprise coupling a semiconductor die 1000 to a first set of conductive terminals 702 (1302). The method 1300 may comprise housing the semiconductor die 1000 and the first set of conductive terminals 702 in a package 700, with a fluid sensing portion 701 of the semiconductor die 1000 exposed external to the package 700 (1304). The method 1300 may comprise positioning the package 700 in a socket 500 such that the first set of conductive terminals 702 electrically couples with a second set of conductive terminals 512 of the socket 500, where the second set of conductive terminals 512 electrically couple to a testing device 1108 (1306). The method 1300 may comprise closing and latching a lid 504 of the socket 500 after positioning the package 700 within the socket 500, thereby positioning a ring 106 of a fluid probe 100 on the fluid sensing portion 701 (1308). The ring 106 may be positioned relative to the socket 500 using a counterscrew member 200 and/or an adapter member 300. The method 1300 may comprise electrically coupling the second set of conductive terminals 512 to the testing device 1108 (1310). The method 1300 may comprise generating a pressure differential between a distal fluid inlet 116 and a distal fluid outlet 118 of the fluid probe 100 (1312). The method 1300 may comprise using the pressure differential to cause fluid to flow through the distal fluid inlet 116, to be applied to an area of the fluid sensing portion 701 circumscribed by the ring 106, and to flow through the distal fluid outlet 118 (1314). The method 1300 may comprise receiving a signal from the semiconductor die 1000 at the testing device 1108, the signal indicative of a property of the fluid (1316). The method 1300 may comprise comparing the property indicated by the signal to an expected property (1318). The method 1300 may comprise unlatching and opening the lid 504 of the socket 500 (1320). The method 1300 may comprise removing the semiconductor die 1000 from the socket 500 (1322). Steps may be added, removed, modified, or rearranged as desired and as may be appropriate.

The above discussion is meant to be illustrative of the principles and various embodiments of the present disclosure. Numerous variations and modifications will become apparent to those skilled in the art once the above disclosure is fully appreciated. It is intended that the following claims be interpreted to embrace all such variations and modifications.

What is claimed is:

1. A system, comprising:
   a fluid probe body comprising first and second threaded cavities;
   a threaded extension coupled to the fluid probe body;
   a distal fluid inlet extending through the fluid probe body and the threaded extension, the distal fluid inlet meeting the first threaded cavity at an inlet interface;
   a distal fluid outlet extending through the fluid probe body and the threaded extension, the distal fluid outlet meeting the second threaded cavity at an outlet interface;
   a ring coupled to an end of the threaded extension that is distal to the fluid probe body, a fluid inlet orifice of the distal fluid inlet circumscribed by the ring, a fluid outlet orifice of the distal fluid outlet circumscribed by the ring; and
   a socket containing a semiconductor die coupled to the threaded extension via an adapter member, the adapter member screwed to the threaded extension and to a lid of the socket.

2. The system of claim 1, wherein the ring extends through a probe orifice in the socket.

3. The system of claim 1, further comprising a fluid inlet member positioned inside the first threaded cavity, the fluid inlet member comprising a proximal fluid inlet.

4. The system of claim 1, further comprising a fluid outlet member positioned inside the second threaded cavity, the fluid outlet member comprising a proximal fluid outlet.

5. The system of claim 1, further comprising a counterscrew member coupled to the threaded extension.

6. The system of claim 1, wherein the fluid probe is mounted on a lid of the socket.

7. The system of claim 6, wherein an adapter member is positioned on the lid of the socket and the fluid probe extends through the adapter member.

8. The system of claim 7, wherein the fluid probe extends through a counterscrew member.

9. A system, comprising:
a fluid probe body;
a ring coupled to a distal end of the fluid probe body, a fluid inlet orifice of the fluid probe body circumscribed by the ring, a fluid outlet orifice of the fluid probe body circumscribed by the ring; and
a socket containing a mounting position for a semiconductor die, the ring for sealing the fluid probe body to a surface of the semiconductor die, wherein a lid of the socket is latched over the semiconductor die after the semiconductor die is positioned within the socket.

10. The system of claim 9, wherein the ring seals the fluid probe body to a fluid sensing portion of the semiconductor die.

11. The system of claim 10, wherein the fluid probe is enabled to apply fluid to an area of the fluid sensing portion circumscribed by the ring.

12. The system of claim 9, wherein the fluid probe comprises polyetheretherketone (PEEK).

13. The system of claim 9, further comprising a testing device enabled to send test signals to the semiconductor device.

14. The system of claim 13, wherein the testing device is enabled to receive a signal from the semiconductor die, the signal indicative of a property of the fluid.

15. The system of claim 14, wherein the testing device is enabled to compare the property indicated by the signal to an expected property.

16. The system of claim 9, wherein the fluid probe is mounted on the lid of the socket.

17. The system of claim 16, wherein an adapter member is positioned on the lid of the socket and the fluid probe extends through the adapter member.

18. The system of claim 9, further comprising generating a pressure differential between the fluid inlet and the fluid outlet.

19. The system of claim 18, further comprising using the pressure differential to cause the fluid to flow through the distal fluid inlet, to an area, and through the distal fluid outlet.

20. A system, comprising:
a fluid probe body;
a ring coupled to a distal end of the fluid probe body, a fluid inlet orifice of the fluid probe body circumscribed by the ring, a fluid outlet orifice of the fluid probe body circumscribed by the ring;
a socket containing a mounting position for a semiconductor die, the ring for sealing the fluid probe body to a surface of the semiconductor die;
wherein the ring seals the fluid probe body to a fluid sensing portion of the semiconductor die;
wherein the fluid probe is enabled to apply fluid to an area of the fluid sensing portion circumscribed by the ring; and
wherein the socket comprises a set of conductive terminals for coupling to terminals on the semiconductor die.

21. The system of claim 20, wherein the conductive terminals are further connected to a testing device.

22. The system of claim 21, wherein the testing device is enabled to send test signals to the semiconductor device.

23. The system of claim 22, wherein the testing device is enabled to receive a signal from the semiconductor die, the signal indicative of a property of the fluid.

24. The system of claim 23, wherein the testing device is enabled to compare the property indicated by the signal to an expected property.

25. A system, comprising:
a fluid probe body;
a ring coupled to a distal end of the fluid probe body, a fluid inlet orifice of the fluid probe body circumscribed by the ring, a fluid outlet orifice of the fluid probe body circumscribed by the ring;
a socket containing a mounting position for a semiconductor die, the ring for sealing the fluid probe body to a surface of the semiconductor die;
wherein the ring seals the fluid probe body to a fluid sensing portion of the semiconductor die;
wherein the fluid probe is enabled to apply fluid to an area of the fluid sensing portion circumscribed by the ring; and
wherein the fluid probe comprises a distal fluid inlet and a distal fluid outlet oriented at an angle relative to the distal fluid inlet, the distal fluid inlet and the distal fluid outlet meeting at the ring.

26. The system of claim 25, further comprising generating a pressure differential between the distal fluid inlet and the distal fluid outlet.

27. The system of claim 26, further comprising using the pressure differential to cause the fluid to flow through the distal fluid inlet, to the area, and through the distal fluid outlet.

28. A system, comprising:
a semiconductor die coupled to a first set of conductive terminals;
a package housing the semiconductor die and the first set of conductive terminals, a fluid sensing portion of the semiconductor die exposed external to the package;
a socket for receiving the package such that the first set of conductive terminals electrically couples with a second set of conductive terminals of the socket, the second set of conductive terminals electrically coupled to a testing device;
a fluid probe positioned on the fluid sensing portion;
a testing device for receiving data from the semiconductor die;
the fluid probe mounted on the socket and extending through a probe orifice in the socket, the fluid probe comprising a distal fluid inlet and a distal fluid outlet, the distal fluid inlet and the distal fluid outlet having fluid inlet and fluid outlet orifices, respectively, located at a ring of the fluid probe;
the distal fluid inlet enabled to apply fluid to an area of the fluid sensing portion circumscribed by the ring; and
the distal fluid outlet enabled to remove the fluid from the area.

29. The system of claim 28, wherein the fluid probe comprises a main body and a threaded extension, the threaded extension extending through the probe orifice in the socket.

30. The system of claim 29, wherein the threaded extension extends through a counterscrew member and an adapter member, the adapter member fastened to the socket.

31. The system of claim 30, wherein the counterscrew member and the adapter member are positioned between the socket and the main body.

32. A system, comprising:
- a semiconductor die electrically coupled to a first set of conductive terminals;
- a second set of conductive terminals in a socket electrically connecting the first set of conductive terminals to a testing device;
- a fluid probe mounted on a lid of the socket and extending through the lid of the socket, the fluid probe including a distal fluid inlet, a distal fluid outlet positioned at an angle with respect to the distal fluid inlet, and a ring at which the distal fluid inlet and the distal fluid outlet meet, the ring positioned on a fluid sensing portion of the semiconductor die;
- a pump for pumping fluid to an area of the fluid sensing portion circumscribed by the ring and for removing the fluid from the area of the fluid sensing portion;
- a testing device for receiving a signal from the semiconductor die at the testing device, the signal indicative of a property of the fluid.

33. The system of claim 32, wherein the ring is positioned relative to the socket using an adapter member, the adapter member fastened to the lid of the socket, the fluid probe extending through the adapter member.

34. The system of claim 33, wherein a counterscrew member positions the ring relative to the socket, the fluid probe extending through the counterscrew member.

* * * * *